United States Patent

Esanu

[11] Patent Number: 4,602,020
[45] Date of Patent: Jul. 22, 1986

[54] 6-AMINOMETHYL-FURO-(3,4-C)-PYRIDINE DERIVATIVES AND THERAPEUTIC COMPOSITIONS CONTAINING THE SAME

[75] Inventor: André Esanu, Paris, France

[73] Assignee: Societe de Conseils de Recherches et d'Applications Scientifiques (S.C.R.A.S.), Paris, France

[21] Appl. No.: 742,556

[22] Filed: Jun. 7, 1985

[30] Foreign Application Priority Data

Jun. 7, 1984 [GB] United Kingdom ............... 8414559

[51] Int. Cl.$^4$ ................. A61K 31/395; C07D 491/02
[52] U.S. Cl. .................................. 514/302; 546/116
[58] Field of Search ............... 546/116; 544/60, 126; 514/302

[56] References Cited

U.S. PATENT DOCUMENTS 3,763,173  9/1973  Barth ............................ 546/116
4,448,962  5/1984  Irikura et al. ................. 546/156

OTHER PUBLICATIONS

Morrison and Boyd Org. Chem. 3rd Ed. p. 746.

Primary Examiner—Henry R. Jiles
Assistant Examiner—J. Richter
Attorney, Agent, or Firm—Lucas & Just

[57] ABSTRACT

This invention relates to 1,3 - dihydro-6-aminomethyl-7-hydroxy-furo-(3,4-c)- pyridine derivatives of the general formula I

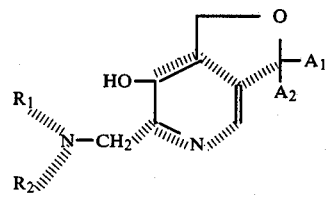

wherein $A_1$, $A_2$, $R_1$ and $R_2$ represent various substituents, to pharmaceutically acceptable salts of such compounds, to a process for the preparation of compounds comprising reacting a 6-chloromethyl-7-benzoxy derivative of the general formula II

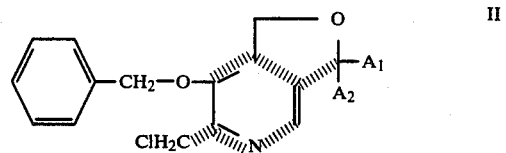

with an excess of an amine derivative

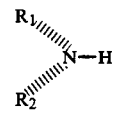

in a non-polar solvent, at a temperature not exceeding 20° C., which leads to the desired substitution in position 6, followed by an acidic treatment to cleave the benzyl group and, finally to an anti-allergic composition of matter comprising, as an essential ingredient therein, an effective amount of one of these compounds together with an appropriate diluent or carrier.

3 Claims, No Drawings

6-AMINOMETHYL-FURO-(3,4-C)-PYRIDINE DERIVATIVES AND THERAPEUTIC COMPOSITIONS CONTAINING THE SAME

The invention relates to 6-aminomethyl-furo-(3,4-c)-pyridine derivatives, to a process for their preparation and to pharmaceutical compositions containing them.

The invention provides 1,3-dihydro-6-aminomethyl-7-hydroxy-furo-(3,4-c)-pyridine derivatives of the general formula I

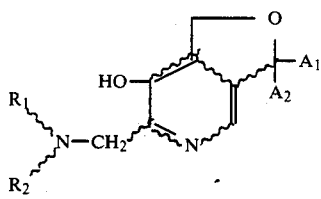

wherein each of $A_1$ and $A_2$ independently represents a hydrogen atom, a straight chain saturated or unsaturated hydrocarbon group having from 1 to 5 carbon atoms, a heterocyclic group having up to 6 ring atoms, a carbomonocylic group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or $\alpha$- or $\beta$-alkoxy-N-pyrrolidinyl groups in which the alkoxy group has from 1 to 5 carbon atoms; and each of $R_1$ and $R_2$ independently represents a hydrogen atom, a methyl group or an ethyl group, with the proviso that $R_1$ and $R_2$ do not simultaneously represent hydrogen atoms or together with the nitrogen atom, form a pyrrolidine, piperidine, morpholine or thiomorpholine ring; and further provides pharmaceutically acceptable salts of such compounds.

The compounds according to the invention are of interest for their therapeutical activity, principally in the field of antiallergic action.

The invention also provides a process for the preparation of the compounds according to the invention, the process comprising reacting a 6-chloromethyl-7-benzoxy derivative of the general formula II

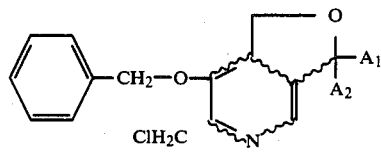

wherein $A_1$ and $A_2$ have the above meanings with an excess of an amine derivative of the general formula IV

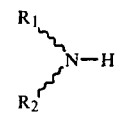

wherein $R_1$ and $R_2$ have the above meanings, in a nonpolar solvent, at a temperature not exceeding 20° C., which leads to the desired substitution in position 6, followed by an acidic treatment to cleave the benzyl group. The excess of the amine derivative IV is necessary for this family of compounds consists of gases or low temperature boiling liquids.

The 6-chloromethyl-7-benzoxy derivatives II may be obtained from corresponding 6-methyl-7-hydroxy derivatives of the general formula III

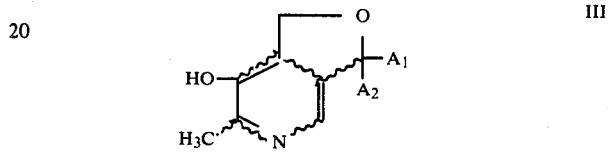

wherein $A_1$ and $A_2$ have the above meanings by the following sequence of reactions:

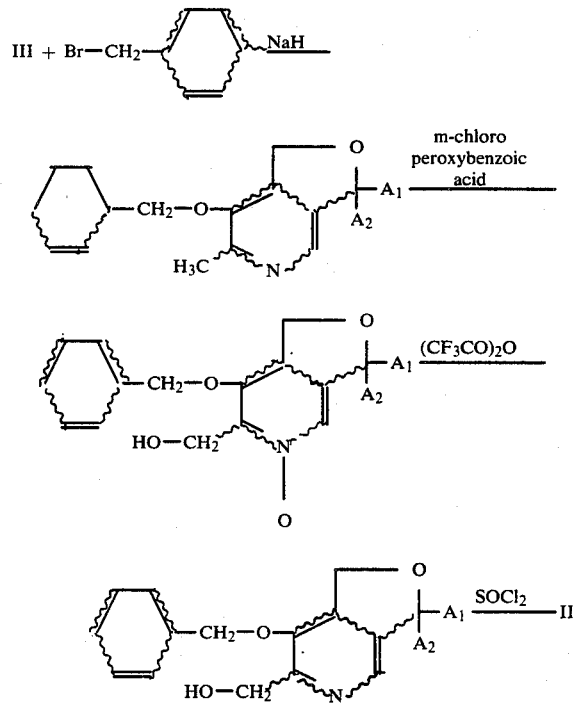

The compounds II are disclosed in our U.S. Pat. No. 4,383,998 and patent application Ser. No. 593,700.

The preparation of one only of the starting compounds, 1,3-dihydro-3-p-chlorophenyl-6-chloromethyl-7-benzoxy-furo-(3,4-c)-pyridine, is now described in detail, other starting materials being obtained by the same way.

(a) Into a one liter reactor fitted with stirring, warming and cooling means were poured 400 ml of dimethylformamide, 12.5 g of 50% sodium hydride and slowly, under stirring 38 g of 1,3-dihydro-3-p-chlorophenyl-6- methyl-7-hydroxy-furo-(3,4-c)-pyridine. After stirring for 90 minutes at room temperature there were added 16 ml of benzyl bromide and the resultant suspension was stirred overnight. After evaporation to dryness, the pasty product obtained was stirred with one liter of methylene dichloride, washed with water until complete elimination of chlorine and bromine and dried on anhydrous sodium sulphate. The methylene dichloride was evaporated off and the residue was dissolved in isopropanol at the boil, treated with carbon black and warm filtered, and then recrystallized. It was washed with petroleum ether and dried. Yield 33 g (74%) of 1,3-dihydro-3-p-chlorophenyl-6-methyl-7-benzoxy-furo-(3,4-c)-pyridine.

(b) In the same reactor as above, 30 g of the product of previous step were treated at 0° C., in the presence of 300 ml of methylene dichloride, with 18.2 g of m-peroxybenzoic acid, slowly added. After stirring overnight at room temperature, there were added 150 ml of 10% sodium sulphite solution. After stirring and decantation, the product was washed with the same amount of sodium sulphite solution, twice with 150 ml of sodium bicarbonate solution and three times with 100 ml of water, and then dried over anhydrous sodium sulphate. On evaporation to dryness, there was obtained a beige precipitate which was washed with petroleum ether, filtered and dried. Yield 28 g (90%) of 1,3-dihydro-3-p-chlorophenyl-6-methyl-7-benzoxy-furo-(3,4-c)-pyridine-N-oxide.

(c) In the same reactor as above, 28 g of the compound obtained in the previous step were treated at 0°–5° C., in the presence of 175 ml of methylene dichloride, with 4.3 ml of trifluoroacetic anhydride added dropwise under stirring. The mixture was stirred overnight at room temperature, and then cooled and treated dropwise with 95 ml of methanol. After evaporation to dryness, the residue was taken up in 300 ml of chloroform, washed twice with 75 ml of 10% sodium bicarbonate solution and three times with 100 ml of water and dried on anhydrous sodium sulphate. The chloroform was evaporated off and the residue was washed with diethyl ether and dried under reduced pressure. Yield 25 g (89%) of 1,3-dihydro-3-p-chlorophenyl-6-hydroxy-methyl-7-benzoxy-furo-(3,4-c)-pyridine.

(d) In a two liter reactor fitted as above and under nitrogen circulation, 25 g of the previously obtained compound were stirred with 400 ml of dry benzene; there were slowly added 6.3 ml of thionyl chloride under stirring at room temperature. The resultant mixture was warmed at 70° C. for one hour, leading to a yellow precipitate. This was separated off, washed with benzene and then diethyl ether, and dissolved in 400 ml of methylene dichloride. The solution was washed with 10% sodium bicarbonate solution until pH 8, washed with water, treated with carbon black, filtered, and concentrated up to recrystallization. The product was separated off, washed with diethyl ether and dried, giving 254 g (yield 92%) of 1,3-dihydro-3-p-chlorophenyl-6-chloromethyl-7-benzoxy-furo-(3,4-c)-pyridine.

The invention further provides a pharmaceutical composition comprising a 1,3-dihydro-6-aminomethyl-7-hydroxy-furo-(3,4-c)-pyridine derivative of the general formula I as above defined or a pharmaceutically acceptable salt thereof in admixture with a pharmaceutically acceptable diluent or carrier.

The invention is illustrated by the following examples.

EXAMPLE 1

1,3-dihydro-3-methyl-6-dimethylaminomethyl-7-hydroxy-furo-(3,4-c)-pyridine

Using the same apparatus as above, 14.5 g (0.05 mol) of 1,3-dihydro-3-methyl-6-chloromethyl-7-benzoxy-furo-(3,4-c)-pyridine were suspended in 100 ml of benzene at 10° C. There was then added a solution of 10 ml of dimethylamine in 100 ml of benzene. The mixture was stirred for 2 hours, leading to a solution which precipitates on being allowed to return to room temperature. The dry residue was recrystallized using 160 ml of isopropanol, and dried. Yield 87% of the benzoxy derivative, which was then treated with 340 ml of 2N hydrochloric acid under stirring for 3 hours. After evaporation to dryness, there were obtained 9.29 g of 1,3-dihydro-3-methyl-6-dimethylaminomethyl-7-hydroxy-furo-(3,4-c)-pyridine as an oily product. Elemental analysis showed good correspondence with the formula $C_{11}H_{16}N_2O_2.HCl$. The overall yield of this sequence of reactions was 76%.

EXAMPLE 2

1,3-dihydro-3-propyl-6-methylaminomethyl-7-hydroxy-furo-(3,4-c)-pyridine

The method of example 1 was repeated, but starting with 1,3-dihydro-3-propyl-6-chloromethyl-7-benzoxy-furo-(3,4-c)-pyridine and gaseous methylamine dissolved in benzene. Yield 66% of an oily product, elemental analysis of which showed good correspondence with the formula $C_{12}H_{18}N_2O_2.HCl$.

EXAMPLE 3

1,3-dihydro-3-phenyl-6-dimethylaminomethyl-7-hydroxy-furo-(3,4-c)-pyridine

The method of example 1 was repeated, but starting with 1,3-dihydro-3-phenyl-6-chloromethyl-7-benzoxy-furo-(3,4-c)-pyridine. Yield 66% of a pale yellow crystalline product melting at 196°–209° C. (Tottoli), elemental analysis of which showed good correspondence with the formula $C_{16}H_{18}N_2O_2.2HCl$.

EXAMPLE 4

1,3-dihydro-3-p-chlorophenyl-6-dimethylaminomethyl-7-hydroxy-furo-(3,4-c)-pyridine The method of example 1 was repeated, but starting with 1,3-dihydro-3-p-chlorophenyl-6-chloromethyl-7-benzoxy-furo-(3,4-c)-pyridine. Yield 49% of a product melting at 207°–211° C. (Tottoli), elemental analysis of which showed good correspondence with the formula $C_{16}H_{17}N_2O_2Cl.2HCl$.

EXAMPLE 5

1,3-dihydro-3-p-fluorophenyl-6-dimethylaminomethyl-7-hydroxy-furo-(3,4-c)-pyridine The method of example 1 was repeated, but starting with 1,3-dihydro-3-p-fluorophenyl-6-chloromethyl-7-benzoxy-furo-(3,4-c)-pyridine. Yield 57% of a light beige product melting at 215°–220° C. (Tottoli), elemental analysis of which showed good correspondence with the formula $C_{16}H_{17}N_2O_2F.2HCl$.

EXAMPLE 6

1,3-dihydro-3-phenyl-6-methylaminomethyl-7-hydroxy-furo-(3,4-c)-pyridine

The method of example 2 was repeated, but starting with 1,3-dihydro-3-phenyl-6-chloromethyl-7-benzoxy-furo-(3,4-c)-pyridine. Yield 45% of a grey-green product melting at 190°–205° C. (Tottoli), elemental analysis of which showed good correspondence with the formula $C_{15}H_{16}N_2O_2.2HCl$.

EXAMPLE 7

1,3-dihydro-3-p-chlorophenyl-6-methylaminomethyl-7-hydroxy-furo-(3,4-c)-pyridine The method of example 2 was repeated, but starting with 1,3-dihydro-3-p-chlorophenyl-6-chloromethyl-7-benzoxy-furo-(3,4-c)-pyridine. Yield 61% of a light yellow powder melting at 198° C. (Tottoli), elemental analysis of which showed good correspondence with the formula $C_{15}H_{15}N_2O_2Cl.2HCl$.

EXAMPLE 8

1,3-dihydro-3-p-fluorophenyl-6-methylaminomethyl-7-hydroxy-furo-(3,4-c)-pyridine The method of example 2 was repeated, but starting with 1,3-dihydro-3-p-fluorophenyl-6-chloromethyl-7-benzoxy-furo-(3,4-c)-pyridine. Yield 54% of a yellow powder melting at 228°–230° C. (Tottoli), elemental analysis of which showed good correspondence with the formula $C_{15}H_{15}N_2O_2F.2HCl$.

EXAMPLE 9

1,3-dihydro-3-phenyl-6-pyrrolidinomethyl-7-hydroxy-furo-(3,4-c)-pyridine

The method of example 3 was repeated, but starting with pyrrolidine instead of dimethylamine. Yield 77% of a pale yellow crystalline product melting at 107° C. (Tottoli), elemental analysis of which showed a good correspondence with the formula $C_{18}H_{20}N_2O_4$.

EXAMPLE 10

1,3-dihydro-3-phenyl-6-piperidinomethyl-7-hydroxy-furo-(3,4-c)-pyridine

The method of example 9 was repeated, but starting with piperidine instead of pyrrolidine. Yield 66% of a pale beige crystalline product melting at 138° C. (Tottoli), elemental analysis of which showed a good correspondence with the formula $C_{19}H_{22}N_2O_2$.

EXAMPLE 11

1,3-dihydro-3-phenyl-6-morpholinomethyl-7-hydroxy-furo-(3,4-c)-pyridine

The method of example 9 was repeated, but starting with morpholine instead of pyrrolidine. Yield 72% of a white powder melting at 172° C. (Tottoli), elemental analysis of which showed good correspondence with the formula $C_{18}H_{20}N_2O_3$.

EXAMPLE 12

1,3-dihydro-3-phenyl-6-thiomorpholinomethyl-7-hydroxy-furo-(3,4-c)-pyridine

The method of example 11 was repeated, but starting with thiomorpholine instead of morpholine. Yield 58% of a white grey powder melting at 185° C. (Tottoli), elemental analysis of which showed a good correspondence with the formula $C_{18}H_{20}N_2O_2S$.

EXAMPLE 13

1,3-dihydro-3,3-dimethyl-6-dimethylaminomethyl-7-hydroxy-furo-(3,4-c)-pyridine

The method of example 1 was repeated, but starting with 1,3-dihydro-3,3-dimethyl-6-chloromethyl-7-benzoxy-furo-(3,4-c)-pyridine. Yield 53% of a pale yellow crystalline product melting at 175° C. (Tottoli), elemental analysis of which showed a good correspondence with the formula $C_{13}H_{20}N_2O_2.2HCl$.

EXAMPLE 14

1,3-dihydro-3-methyl-3-n-butyl-6-dimethylaminomethyl-7-hydroxy-furo-(3,4-c)-pyridine The method of example 1 was repeated, but starting with 1,3-dihydro-3-methyl-3-n-butyl-6-chloromethyl-7-benzoxy-furo-(3,4-c)-pyridine and dimethylamine dissolved in benzene. Yield 48% of an oily product, elemental analysis of which showed a good correspondence with the formula $C_{14}H_{22}N_2O_2.HCl$.

EXAMPLE 15

1,3-dihydro-3-ethyl-3-p-chlorophenyl-6-dimethylaminomethyl-7-hydroxy-furo-(3,4-c)-pyridine The method of example 1 was repeated, but starting with 1,3-dihydro-3-ethyl-3-p-chlorophenyl-6-chloromethyl-7-benzoxy-furo-(3,4-c)-pyridine. Yield 64% of a product melting at 151° C. (Tottoli), elemental analysis of which showed good correspondence with the formula $C_{18}H_{21}N_2O_2Cl.2HCl$.

EXAMPLE 16

1,3-dihydro-3-phenyl-3-p-fluorophenyl-6-dimethylaminomethyl-7-hydroxy-furo-(3,4-c)-pyridine The method of example 1 was repeated, but starting with 1,3-dihydro-3-phenyl-3-p-fluorophenyl-6-chloromethyl-7-benzoxy-furo-(3,4-c)-pyridine. Yield 44% of a beige product melting at 184° C. (Tottoli), elemental analysis of which showed good correspondence with the formula $C_{22}H_{21}N_2O_2F.2HCl$.

EXAMPLE 17

1,3-dihydro-3-α-furyl-3-phenyl-6-methylaminomethyl-7-hydroxy-furo-(3,4-c)-pyridine The method of example 2 was repeated, but starting with 1,3-dihydro-3-α-furyl-3-phenyl-6-chloromethyl-7-benzoxy-furo-(3,4-c)-pyridine. Yield 42% of a white crystalline product melting at 191°–193° C. (Tottoli), elemental analysis of which showed good correspondence with the formula $C_{19}H_{18}N_2O_3.2HCl$.

EXAMPLE 18

1,3-dihydro-3-p-trifluoromethylphenyl-3-p-chlorophenyl-6-methylaminomethyl-7-hydroxy-furo-(3,4-c)-pyridine The method of example 3 was repeated, but starting with 1,3-dihydro-3-p-trifluoromethylphenyl-3-p-chlorophenyl-6-chloromethyl-7-benzoxy-furo-(3,4-c)-pyridine. Yield 59% of a yellow powder melting at 178° C. (Tottoli), elemental analysis of which showed good correspondence with the formula $C_{22}H_{19}N_2O_2F_3Cl.2HCl$.

EXAMPLE 19

1,3-dihydro-3-α-thienyl-3-p-fluorophenyl-6-methylaminomethyl-7-hydroxy-furo-(3,4-c)-pyridine The method of example 2 was repeated, but starting with 1,3-dihydro-3-α-thienyl-3-p-fluorophenyl-6-chloromethyl-7-benzoxy-furo-(3,4-c)-pyridine. Yield 55% of a yellow powder melting at 184°–189° C. (Tottoli), elemental analysis of which showed good correspondence with the formula $C_{19}H_{17}N_2O_2SF.2HCl$.

EXAMPLE 20

1,3-dihydro-3-cyclohexyl-3-phenyl-6-pyrrolidinomethyl-7-hydroxy-furo-(3,4-c)-pyridine The method of example 3 was repeated, but starting with 1,3-dihydro-3-cyclohexyl-3-phenyl-6-chloromethyl-7-benzoxy-furo-(3,4-c)-pyridine and with pyrrolidine instead of dimethylamine. Yield 67% of a yellow crystalline product melting at 204° C. (Tottoli), elemental analysis of which showed a good correspondence with the formula $C_{24}H_{30}N_2O_4$.

EXAMPLE 21

1,3-dihydro-3-methyl-3-p-dimethylaminoethoxyphenyl-6-piperidinomethyl-7-hydroxy-furo-(3,4-c)-pyridine The method of example 10 was repeated, but starting with 1,3-dihydro-3-methyl-3-p-dimethylaminoethoxyphenyl-6-chloromethyl-7-benzoxy-furo-(3,4-c)-pyridine. Yield 38% of a beige crystalline product melting at 116° C. (Tottoli), elemental analysis of which showed a good correspondence with the formula $C_{24}H_{33}N_2O_2$.

EXAMPLE 22

1,3-dihydro-3-ethyl-3-dimethylaminopropyl-6-morpholinomethyl-7-hydroxy-furo-(3,4-c)-pyridine The method of example 11 was repeated, but starting with 1,3-dihydro-3-ethyl-3-dimethylaminopropyl-6-chloromethyl-7-benzoxy-furo-(3,4-c)-pyridine. Yield 42% of a white product melting at 167° C. (Tottoli), elemental analysis of which showed a good correspondence with the formula $C_{19}H_{30}N_3O_3$.

EXAMPLE 23

1,3-dihydro-3-n-pentyl-3-(3,4,5-trimethoxy)-phenyl-6-thiomorpholinomethyl-7-hydroxy-furo-(3,4-c)-pyridine The method of example 12 was repeated, but starting with 1,3-dihydro-3-n-pentyl-3-(3,4,5-trimethoxy)-phenyl-6-chloromethyl-7-benzoxy-furo-(3,4-c)-pyridine. Yield 48% of a white powder melting at 149° C. (Tottoli), elemental analysis of which showed a good correspondence with the formula $C_{26}H_{36}N_2O_2S$.

EXAMPLE 24

1,3-dihydro-3,3-di-alpha-furyl-6-methylaminomethyl-7-hydroxy-furo-(3,4-c)-pyridine The method of example 12 was repeated, but starting with 1,3-dihydro-3,3-di-alpha-furyl-6-chloromethyl-7-benzoxy-furo-(3,4-c)-pyridine. Yield 62% of a white crystalline product melting at 176°–179° C. (Tottoli), elemental analysis of which showed good correspondence with the formula $C_{17}H_{16}N_2O_4.2HCl$.

EXAMPLE 25

1,3-dihydro-3-phenyl-3-(3,4,5-trimethoxy)-phenylethyl-6-dimethylaminomethyl-7-hydroxy-furo-(3,4-c)-pyridine The method of example 1 was repeated, but starting with 1,3-dihydro-3-phenyl-3-(3,4,5-trimethoxy)-phenylethyl-6-chloromethyl-7-benzoxy-furo-(3,4-c)-pyridine. Yield 31% of a grey product melting at 163°–166° C. (Tottoli), elemental analysis of which showed good correspondence with the formula $C_{27}H_{32}N_2O_2.2HCl$.

EXAMPLE 26

1,3-dihydro-3-methyl-3-(p-pyrrolidinylethoxy)-phenyl-6-dimethylaminomethyl-7-hydroxy-furo-(3,4-c)-pyridine The method of example 1 was repeated, but starting with 1,3-dihydro-3-methyl-3-(p-pyrrolidinylethoxy)-phenyl-6-chloromethyl-7-benzoxy-furo-(3,4-c)-pyridine. Yield 54% of a pale yellow crystalline product melting at 188° C. (Tottoli), elemental analysis of which showed a good correspondence with the formula $C_{24}H_{33}N_3O_3.2HCl$.

EXAMPLE 27

1,3-dihydro-3-p-toluyl-3-p-thiomethylphenyl-6-pyrrolidinomethyl-7-hydroxy-furo-(3,4-c)-pyridine The method of example 9 was repeated, but starting with 1,3-dihydro-3-p-toluyl-3-p-thiomethylphenyl-6-chloromethyl-7-benzoxy-furo-(3,4-c)-pyridine. Yield 63% of a pale yellow crystalline product melting at 174° C. (Tottoli), elemental analysis of which showed a good correspondence with the formula $C_{26}H_{28}N_2O_4S$.

TOXICITY

Toxicity was investigated on rats and mice (acute per os toxicity). As these compounds present a therapeutic activity at doses lower than or about 25 mg/kg a single oral dose of 600 mg/kg was administered, suspended in gum syrup on batches of 20 rats and 20 mice. No death occured.

PHARMACOLOGY

Antiallergic activity was searched on Sprague-Dawley rats of 180-200 g each through the test of passive cutaneous anaphylaxy.

The back of each rat was shaved and each animal received (time: −48 hours) two injections of each 10 ml of homologous immunserum (dilution ½); at time −30', each animal received two injections of histamine (50 μg/kg dissolved in 10 ml/kg of serum), at time 0, each animal received an i.v. injection of antigen (ovalbumine+Evans blue). This resulted in the formation of 4 cutaneous papules characterised by their areas and by the coloration, after extraction for 48 hours by formamide at 65° C. The above treatment applies to control rats. Treated rats were treated similarly except that 10 mg/kg of the compound to be tested were administered per os one hour before i.v. injection (time: −1 hour).

Batches were of 6 animals either for control, a reference compound ketotifene, or for any of the tested compounds (identified by the number of the corresponding example).

The simultaneous treatment by histamine was for determining an eventual antihistaminic action of the compounds of the invention. An antihistaminic action is a defavourable factor in the treatment of allergies. The results, reported in the following table show a good antiallergic activity associated with a favourably low antihistaminic action, which is not the case for the reference compound.

In the table are given, for each tested compound, for immunserum and for histamine papules:

the area of the papules in mm$^2$, followed by the percentage of reduction compared to control; the percentage is followed by * * * for highly significative result, * * for very significative result, * for significative result or N.S. for non significative result and colorimetric absorbtion results, compared to control (arbitrary units) with the percentage of reduction compared to control, with the same convention.

PRESENTATION—POSOLOGY

The compounds of the invention may be presented in tablets, gelatine capsules or suspensions for oral administration, each dose unit containing 250 mg of active ingredient. Posology in human therapy is from 2 to 6 dose units per diem for about one week.

For injectable route, phials contain 100 mg of active ingredient and posology is from 1 to 5 phials per diem for about one week.

Any usual carrier or diluent may be used for the various presentations.

TABLE

| Compounds | Immunserum papules | | Histamine papules | |
|---|---|---|---|---|
| | Area (mm2) % | Colour % | Area (mm2) % | Colour % |
| Control | 84.4 ± 5.73 | 0.377 ± 0.0384 | 120.7 ± 7.40 | 1.213 ± 0.0726 |
| Ketotifene | 46.3 ± 6.26 | 0.226 ± 0.040 | 53.4 ± 2.05 | 0.389 ± 0.0404 |
| | −45.1*** | −39.9* | −55.8*** | −67.9*** |
| 3 | 31.5 ± 7.98 | 0.166 ± 0.0354 | 95.9 ± 5.76 | 0.762 ± 0.0703 |
| | −63*** | −56*** | −20** | −37*** |
| 6 | 32 ± 8.01 | 0.184 ± 0.0372 | 112.7 ± 4.94 | 1.152 ± 0.0609 |
| | −62*** | −51.2*** | −6.6 NS | −5 NS |
| 8 | 40.5 ± 9.02 | 0.236 ± 0.062 | 103.2 ± 6.33 | 1.025 ± 0.0525 |
| | −52*** | −37.5* | −14.5* | −15.4 NS |
| 9 | 41.6 ± 6.49 | 0.190 ± 0.031 | 103.8 ± 2.76 | 0.892 ± 0.0426 |
| | −51*** | −50*** | −14* | −26** |
| 10 | 34.5 ± 8.16 | 0.162 ± 0.0384 | 104.3 ± 4.71 | 0.931 ± 0.0755 |
| | −59*** | −57*** | −14 NS | −23** |
| 11 | 42.1 ± 6.31 | 0.181 ± 0.0192 | 111.5 ± 6.8 | 1.029 ± 0.0499 |
| | −50** | −52*** | −7.6 NS | −15 NS |
| 12 | 32.3 ± 8.08 | 0.154 ± 0.0333 | 111 ± 6.64 | 0.922 ± 0.0544 |
| | −61.7*** | −59.1*** | −8 NS | −24 NS |
| 15 | 49.1 ± 7.23 | 0.199 ± 0.0328 | 105.6 ± 7.06 | 1.076 ± 0.0873 |
| | −41.8*** | −47*** | −12.5 NS | −11.3 NS |
| 20 | 23 ± 4.41 | 0.205 ± 0.0337 | 94.6 ± 5.05 | 1.035 ± 0.0912 |
| | −72.7*** | −45.7*** | −21.6** | −14.7 NS |
| 21 | 35.6 ± 6.33 | 0.223 ± 0.0366 | 107.9 ± 7.63 | 1.043 ± 0.0924 |
| | −57.8*** | −40.9* | −10.6 NS | −14 NS |
| 24 | 57.4 ± 4.12 | 0.194 ± 0.0195 | 127.6 ± 6.25 | 1.128 ± 0.0946 |
| | −32** | −48.5*** | +5.7 NS | −7 NS |

I claim:

1. 1,3-dihydro-6-aminomethyl-7-hydroxy-furo-(3,4-c)-pyridine derivatives of the general formula I

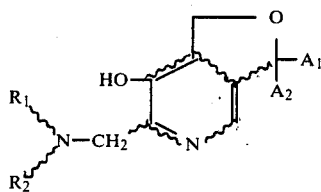

wherein each of $A_1$ and $A_2$ independently represents a hydrogen atom, a straight chain saturated or unsaturated hydrocarbon group having from 1 to 5 carbon atoms, a furyl or thienyl group, a carbomonocyclic group, a phenyloweralkyl group or a phenyloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms; and each of $R_1$ and $R_2$ independently represents a hydrogen atom, a methyl group or an ethyl group, with the proviso that $R_1$ and $R_2$ do not simultaneously represent hydrogen atoms or together with the nitrogen atom, form a pyrrolidine, piperidine, morpholine or thiomorpholine ring; and further provides pharmaceutically acceptable salts of such compounds.

2. A therapeutic composition of matter for treatment of allergy comprising, as an essential ingredient therein, an antiallergically effective amount of a compound according to claim 1 together with a pharmaceutically acceptable diluent or carrier.

3. A method of treating an allergy comprising the administration of an antiallergically effective amount of a compound according to claim 1.

* * * * *

UNITED STATES PATENT AND TRADEMARK OFFICE
CERTIFICATE OF CORRECTION

PATENT NO. : 4,602,020
DATED : July 22, 1986
INVENTOR(S) : Andre Esanu

It is certified that error appears in the above-identified patent and that said Letters Patent is hereby corrected as shown below:

On the front page of the patent, second column, substitute the following formula for the first formula shown:

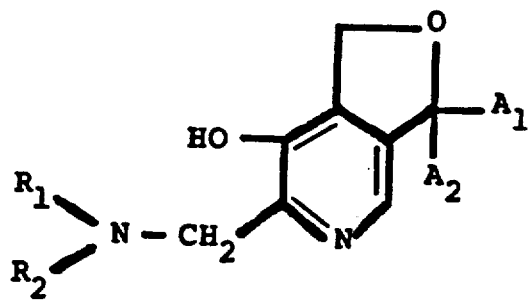

and substitute the following for the second formula shown:

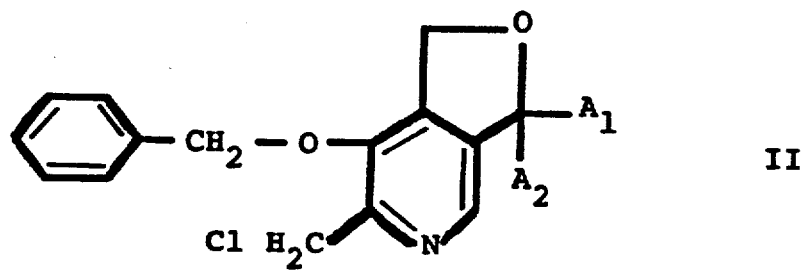

UNITED STATES PATENT AND TRADEMARK OFFICE
CERTIFICATE OF CORRECTION

PATENT NO. : 4,602,020
DATED : July 22, 1986
INVENTOR(S) : Andre Esanu

Page 2 of 6

It is certified that error appears in the above-identified patent and that said Letters Patent is hereby corrected as shown below:

and substitute the following for the third formula shown:

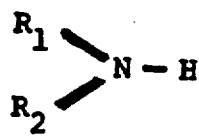

Column 1, lines 12-23, substitute the following for the formula shown:

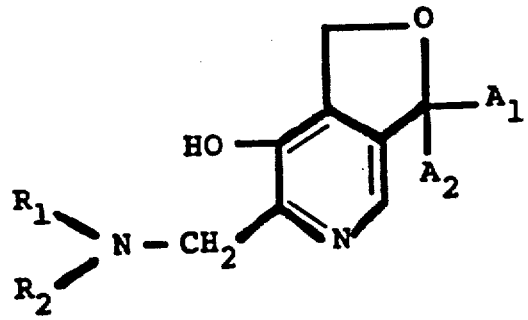

UNITED STATES PATENT AND TRADEMARK OFFICE
CERTIFICATE OF CORRECTION

PATENT NO. : 4,602,020
DATED : July 22, 1986
INVENTOR(S) : Andre Esanu

It is certified that error appears in the above-identified patent and that said Letters Patent is hereby corrected as shown below:

Column 1, lines 54-65, substitute the following for the second formula shown:

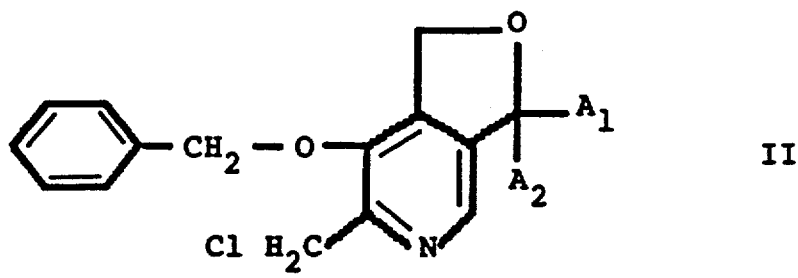

Column 2, lines 1-7, substitute the following for the formula shown:

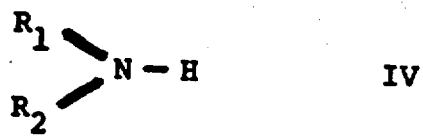

UNITED STATES PATENT AND TRADEMARK OFFICE
CERTIFICATE OF CORRECTION

PATENT NO. : 4,602,020
DATED : July 22, 1986
INVENTOR(S) : Andre Esanu

It is certified that error appears in the above-identified patent and that said Letters Patent is hereby corrected as shown below:

Column 2, lines 18-25, substitute the following for the formula shown:

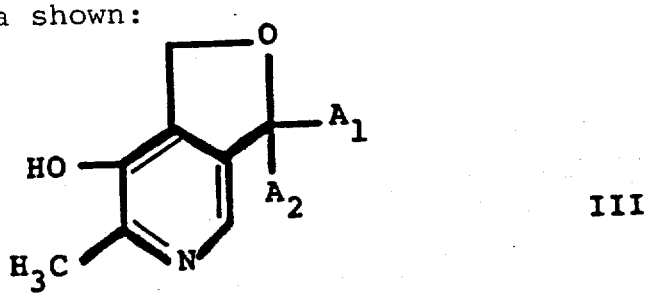

Column 2, lines 28-40, substitute the following for the formulas shown:

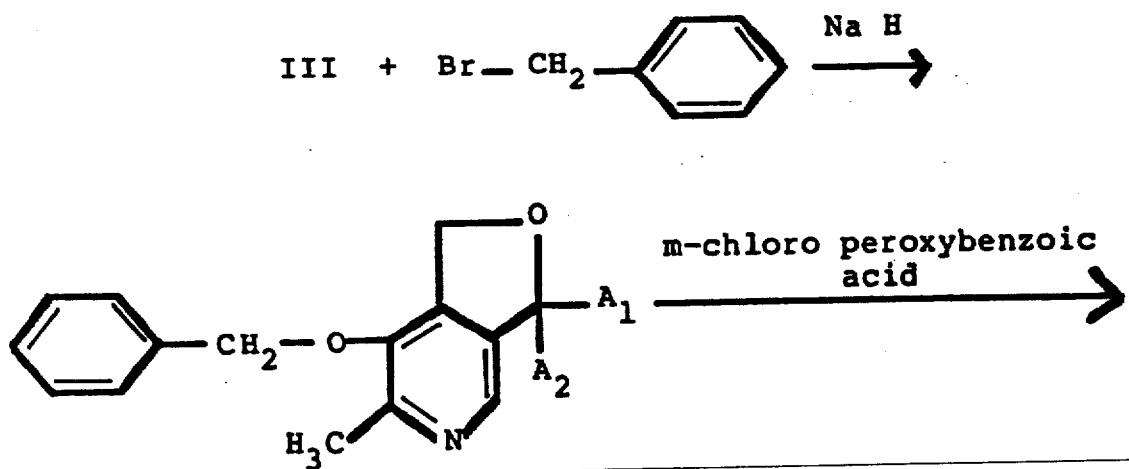

UNITED STATES PATENT AND TRADEMARK OFFICE
CERTIFICATE OF CORRECTION

PATENT NO. : 4,602,020
DATED : July 22, 1986
INVENTOR(S) : Andre Esanu

It is certified that error appears in the above-identified patent and that said Letters Patent is hereby corrected as shown below:

Column 2, lines 41-57, substitute the following for the formulas shown:

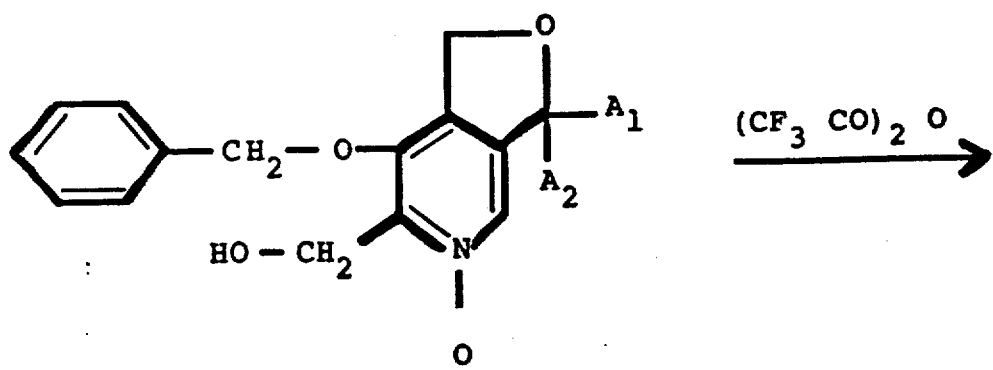

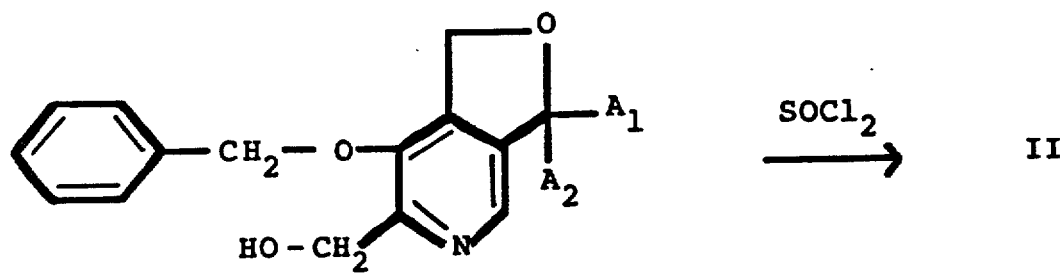

UNITED STATES PATENT AND TRADEMARK OFFICE
CERTIFICATE OF CORRECTION

PATENT NO. : 4,602,020

DATED : July 22, 1986

INVENTOR(S) : Andre Esanu

It is certified that error appears in the above-identified patent and that said Letters Patent is hereby corrected as shown below:

Column 10, lines 1-10 (claim 1), substitute the following for the formula shown:

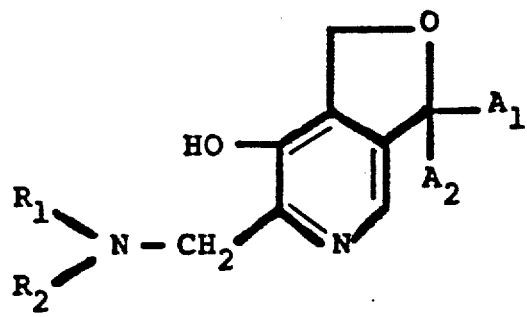

Signed and Sealed this

Twenty-first Day of April, 1987

*Attest:*

DONALD J. QUIGG

*Attesting Officer*   *Commissioner of Patents and Trademarks*